(12) United States Patent
Freeman et al.

(10) Patent No.: US 9,187,433 B2
(45) Date of Patent: Nov. 17, 2015

(54) FORMATION OF N-PROTECTED 3,6-BIS-(4-AMINOBUTYL) -2, 5-DIKETOPIPERAZINE THROUGH A CYCLIC α-N-PROTECTED ACTIVE AMINO ESTER INTERMEDIATE

(71) Applicant: MannKind Corp., Danbury, CT (US)

(72) Inventors: John J. Freeman, New Fairfield, CT (US); Otto Phanstiel, Oviedo, FL (US); William Elliot Bay, Ridgefield, CT (US); Kelly Sullivan Kraft, Poughquag, NY (US)

(73) Assignee: MANNKIND CORPORATION, Valencia, CA (US)

( * ) Notice: Subject to any disclaimer, the term of this patent is extended or adjusted under 35 U.S.C. 154(b) by 0 days.

(21) Appl. No.: 14/629,046

(22) Filed: Feb. 23, 2015

(65) Prior Publication Data

US 2015/0259301 A1 Sep. 17, 2015

Related U.S. Application Data

(63) Continuation of application No. 14/212,957, filed on Mar. 14, 2014, now Pat. No. 8,962,836.

(60) Provisional application No. 61/798,016, filed on Mar. 15, 2013.

(51) Int. Cl.
C07D 241/04 (2006.01)
C07D 241/10 (2006.01)

(52) U.S. Cl.
CPC ............ *C07D 241/04* (2013.01); *C07D 241/10* (2013.01)

(58) Field of Classification Search
USPC .......................................... 544/383
See application file for complete search history.

(56) References Cited

U.S. PATENT DOCUMENTS 8,962,836 B2 * 2/2015 Freeman et al. .............. 544/383

FOREIGN PATENT DOCUMENTS

WO 2006/023849 3/2006
WO 2012/109256 8/2012

OTHER PUBLICATIONS

Byung Hyun Lee and Co. "Constituents of microbial iron chelators. Alternate Syntheses of N-hydroxy-L-ornithine derivatives and applications to the synthesis of rhodotorulic acid" Journal of Organic Chemistry, vol. 49, No. 13, Jan. 1, 1984, p. 2418-2423.
Written Opinion from International Searching Authority for PCT/US2014/028228, 2014.
Office Action from U.S. Appl. No. 14/212,957 dated Jul. 1, 2014.
Notice of Allowance from U.S. Appl. No. 14/212,957 dated Oct. 16, 2014.

* cited by examiner

*Primary Examiner* — Kristin Vajda
(74) *Attorney, Agent, or Firm* — Calfee, Halter & Griswold LLP

(57) ABSTRACT

A method for the synthesis of N-protected 3,6-aminoalkyl-2,5-diketopiperazines is provided. The method includes obtaining a cyclic α-N protected active amino ester and adding it to a mixture of an amine catalyst in an organic solvent.

20 Claims, 4 Drawing Sheets

FORMATION OF N-PROTECTED 3,6-BIS-(4-AMINOBUTYL)-2,5-DIKETOPIPERAZINE THROUGH A CYCLIC α-N-PROTECTED ACTIVE AMINO ESTER INTERMEDIATE

CROSS-REFERENCE TO RELATED APPLICATIONS

This non-provisional patent application claims the benefit of U.S. non-provisional application Ser. No. 14/212,957, filed Mar. 14, 2014, which in-turn claims the benefit of U.S. provisional application No. 61/798,016, filed Mar. 15, 2013, the content of which are hereby incorporated by reference as if recited herein in their entirety.

TECHNICAL FIELD

The present invention relates to compositions for delivering active agents, and particularly biologically active agents. Disclosed embodiments are in the field of chemical synthesis and more particularly are related to improved synthetic methods for the preparation of substituted diketopiperazines.

BACKGROUND

Drug delivery is a persistent problem in the administration of active agents to patients. Conventional means for delivering active agents are often severely limited by biological, chemical, and physical barriers. Typically, these barriers are imposed by the environment through which delivery occurs, the environment of the target for delivery, or the target itself.

Biologically active agents are particularly vulnerable to such barriers. For example in the delivery to humans of pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically active agents would be the route of choice for administration to animals if not for biological, chemical, and physical barriers such as varying pH in the gastrointestinal (GI) tract, powerful digestive enzymes, and active agent impermeable gastrointestinal membranes. Among the numerous agents which are not typically amenable to oral administration are biologically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastrointestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), FEBS Letters, Vol. 62, pg. 60; and Hashimoto et al. (1979), Endocrinology Japan, Vol. 26, pg. 337.

However, broad spectrum use of drug delivery systems is precluded due to a variety of reasons including: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents. One class of delivery system that has shown promise is diketopiperazines. In particular, 3,6-bis-substituted diketopiperazines have been shown to effectively deliver biologically active agents across the lining of the lung.

SUMMARY

This and other unmet needs of the prior art are met by compounds and methods as described in more detail below. The use of 3,6-aminoalkyl-2,5-diketopiperazines as pharmaceutical excipients has shown considerable promise. As mentioned above, diketopiperazines are often synthesized via cyclocondensation of amino acids. If the amino acid has a free nitrogen on its side-chain (as in, for example, lysine or ornithine) it is often necessary to have this nitrogen blocked prior to the cyclization reaction. Compound 1 below shows an example of a N-protected amino acid. Cyclocondensation of 1, under appropriate conditions, then gives compound 2.

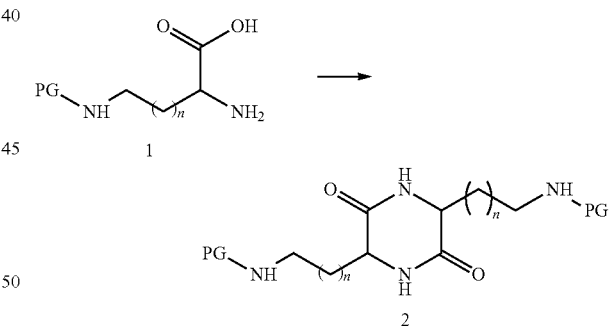

Because of the potential for disparate synthetic processes after diketopiperazine formation, compatibility with a variety of protecting groups is desired. Thus a synthetic method that can accommodate a number of diverse N-protecting groups and produce good yield of N-protected diketopiperazine is desired. However, the cyclocondensation shown often requires high temperatures or harsh conditions to achieve full cyclization. Further, it is not compatible with each N-protecting group that might be necessary for further derivatization of the exo-cyclic nitrogens.

Some useful N-protecting groups include acetyl, trichloroacetyl, trifluoroacteyl and other amide forming protecting groups; carbamate protecting groups including benzyloxycarbonyl (Cbz) and t-butoxycarbonyl (BOC) among others.

In an embodiment, a method for the synthesis of a 3,6-aminoalkyl-2,5-diketopiperazine is provided. The method comprises, adding a cyclic α-N protected active amino ester according to the formula below:

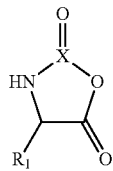

wherein $R_1$ is a N-protected amino $C_1$ to $C_8$ alkyl, and X is C, S or P, to a mixture of an amine catalyst in an organic solvent.

In an embodiment, a method for the synthesis of a 3,6-aminoalkyl-2,5-diketopiperazine is provided. The method comprises, adding a cyclic α-N protected active amino ester to a mixture of an amine catalyst in an organic solvent. In certain embodiments, the method provides 3,6-aminoalkyl-2,5-diketopiperazine in a yield of greater than 40% (i.e., 40 to 100%).

DETAILED DESCRIPTION

Figure 1:
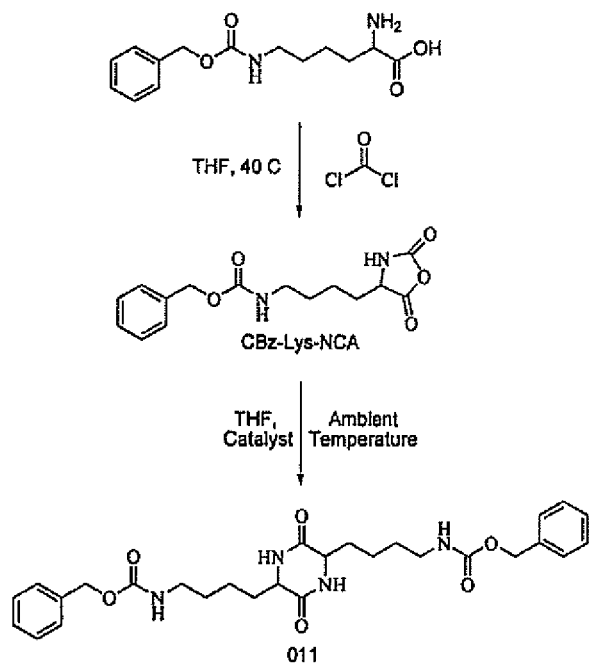
FIG. 1 is a reaction scheme showing an exemplary embodiment of a route for the formation of 3,6-aminoalkyl-2,5-diketopiperazine through a cyclic N-carboxy anhydride (NCA) intermediate.

As used herein, the following terms should be understood as follows: methyl, ethyl, n-Propyl, isopropyl, n-Butyl, isobutyl, sec-butyl, tert-butyl, pentyl, hexyl, heptyl or octyl and all bond isomers are to be considered as $(C_1-C_8)$-alkyl. These can be mono- or poly-substituted with $(C_1-C_8)$-alkoxy, $(C_1-C_8)$-haloalkyl, OH, halogen, $NH_2$, $NO_2$, SH, S—$(C_1-C_8)$-alkyl.

$(C_2-C_8)$-alkenyl, with the exception of methyl, is understood to mean a $(C_1-C_8)$-alkyl group as illustrated above having at least one double bond.

$(C_2-C_8)$-alkynyl, with the exception of methyl, is understood to mean a $(C_1-C_8)$-alkyl group as illustrated above, having at least one triple bond.

$(C_3-C_8)$-Cycloalkyl is understood to mean cyclopropyl, cyclobutyl, cyclopentyl, cyclohexyl or cycloheptyl groups etc. These may be substituted with one or more halogens and/or groups containing N-, O-, P-, S-atoms and/or may have groups containing N-, O-, P-, S-atoms in the ring, such as e.g., 1-,2-,3-,4-piperidyl, 1-,2-,3-pyrrolidinyl, 2-,3-tetrahydrofuryl, 2-,3-,4-morpholinyl. These can also be mono- or poly-substituted with $(C_1-C_8)$-alkoxy, $(C_1-C_8)$-haloalkyl, OH, $C_1$, $NH_2$, $NO_2$.

A $(C_6-C_{18})$-aryl group is understood to be an aromatic group with 6 to 18 C-atoms. These include in particular compounds such as phenyl-, naphthyl-, anthryl-, phenanthryl-, biphenyl groups. It can be mono- or polysubstituted with $(C_1-C_8)$-alkoxy, $(C_1-C_8)$-haloalkyl, OH, halogen, $NH_2$, $NO_2$, SH, S—$(C_1-C_8)$-alkyl.

A $(C_7-C_{19})$-aralkyl group is a $(C_6-C_{18})$-aryl group bound to the molecule by a $(C_1-C_8)$-alkyl group.

$(C_1-C_8)$-alkoxy is a $(C_1-C_8)$-alkyl group bound to the molecule under consideration by an oxygen atom.

$(C_1-C_8)$-haloalkyl is a $(C_1-C_8)$-alkyl group substituted with one or more halogen atoms.

A $(C_3-C_{18})$-heteroaryl group means, in the context of the invention, a five-, six-, or seven-link aromatic ring system of 3 to 18 C atoms, which has heteroatoms such as nitrogen, oxygen or sulfur in the ring. Groups such as 1-,2-,3-furyl, such as 1-,2-,3-pyrrolyl,1-,2-,3-thienyl,2-,3-,4-pyridyl,2-,3-,4-,5-,6-,7-indolyl,3-,4-,5-pyrazolyl,2-,4-,5-imidazolyl, acridinyl, chinolinyl, phenanthridinyl,2-,4-,5-,6-pyrimidinyl are considered in particular to be such heteroatoms. It can be mono- or poly-substituted with $(C_1-C_8)$-alkoxy, $(C_1-C_8)$-haloalkyl, OH, halogen, $NH_2$, $NO_2$, SH, S$(C_1-C_8)$-alkyl.

A $(C_4-C_{19})$-heteroaralkyl is understood to be a heteroaromatic system corresponding to the $(C_7-C_{19})$ aralkyl group.

The term $(C_1-C_8)$-alkylene unit is understood to mean a $(C_1-C_8)$-alkyl group, which is bound to the relevant molecule by two of its C atoms. It can be mono- or poly-substituted with $(C_1-C_8)$-alkoxy, $(C_1-C_8)$-haloalkyl, OH, halogen, $NH_2$, $NO_2$, SH, S—$(C_1-C_8)$-alkyl.

Fluorine, chlorine, bromine and iodine may be considered as halogens.

A side-chain group of an α-amino acid is understood to mean the changeable group on the a-C atom of glycine as the basic amino acid. Natural-amino acids are given for example in Bayer-Walter, Lehrbuch der organischen Chemie, S. Hirzel Verlag, Stuttgart, 22nd edition, page 822ff.

Preferred synthetic α-amino acids are those from DE 19903268.8. The side chain groups can be derived from those referred to there.

The stated chemical structures relate to all possible stereoisomers that can be obtained by varying the configuration of the individual chiral centers, axes or surfaces, in other words all possible diastereomers as well as all optical isomers (enantiomers) falling within this group.

As mentioned above, diketopiperazines are often synthesized via cyclocondensation of amino acids. If the amino acid has a free nitrogen on its side-chain (as in, for example, lysine or ornithine) it is often necessary to have this nitrogen blocked prior to the cyclization reaction. Compound 1 below shows an example of a N-protected amino acid, wherein PG is a protecting group and n denotes a $C_1-C_8$ alkyl. Cyclocondensation of Compound 1, under appropriate conditions, then gives Compound 2.

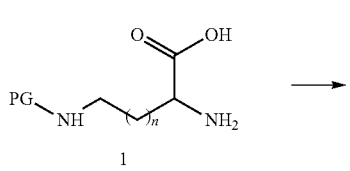

1

-continued

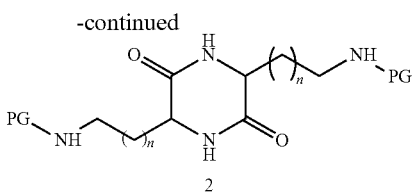

2

Because of the potential for disparate synthetic processes after diketopiperazine formation, compatibility with a variety of protecting groups is desired. Thus a synthetic method that can accommodate a number of diverse N-protecting groups and produce good yield of N-protected diketopiperazine is desired. However, the cyclocondensation shown above often requires high temperatures or harsh conditions to achieve full cyclization. Further, this cyclocondensation is not compatible with each N-protecting group that might be necessary for further derivatization of the exo-cyclic nitrogens (the protected nitrogens).

Some useful N-protecting groups include acetyl, trichloroacetyl, trifluoroacetyl and other amide forming protecting groups; carbamate protecting groups including benzyloxycarbonyl (Cbz) and t-butoxycarbonyl (Boc) among others.

In an embodiment, a method for the synthesis of a 3,6-aminoalkyl-2,5-diketopiperazine is provided. The method comprises, adding a cyclic amino ester according to Compound 3.

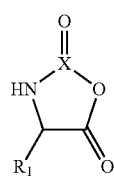

3 wherein $R_1$ is a N-protected amino C1 to C8 alkyl, and X is C, S or P, to a solution of an amine catalyst in an organic solvent.

In an embodiment a method for the synthesis of a N-protected 3,6-bis-aminoalkyl-2,5-diketopiperazine of formula I is provided.

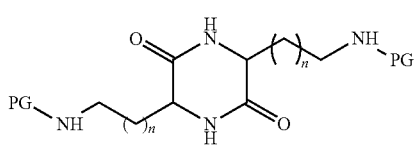

Formula I

The method comprises adding a N-protected cyclic alkyl amino acid according Formula II.

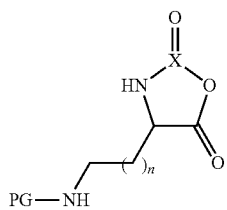

Formula II to a mixture of an amine catalyst in an organic solvent, the amine catalyst selected from the group comprising: aziridine and benzamidoxime.

In certain embodiments, the PG is selected from CBz, Boc, trifluoroacetyl, acetyl and other carbamate and amid forming protecting groups, X is selected from C, S and P, and n is equal to 1 to 8.

In certain embodiments, the synthesis of the diketopiperazine is performed in an organic solvent. Suitable organic solvents include polar organic solvents and non-polar organic solvents. In certain embodiments, the solvent is selected from THF, acetonitrile, dioxane, and ethanol.

In certain embodiments, the synthesis of the diketopiperazine is performed in an organic solvent. Suitable organic solvents include polar organic solvents and non-polar organic solvents. In certain embodiments, the solvent is selected from THF and ethanol.

In certain embodiments, the disclosed methods provide a 3,6-aminoalkyl-2,5-diketopiperazine in a yield of greater than 40% (i.e., 40 to 100%). In certain embodiments, the disclosed methods provide a 3,6-aminoalkyl-2,5-diketopiperazine in a yield of greater than 50% (i.e., 50 to 100%). In certain embodiments, the disclosed methods provide a 3,6-aminoalkyl-2,5-diketopiperazine in a yield of greater than 55% (i.e., 55 to 100%) or more.

In certain embodiments, the disclosed methods provide a 3,6-aminoalkyl-2,5-diketopiperazine having a purity of greater than 70% (i.e., 70 to 100%). In certain embodiments, the disclosed methods provide a 3,6-aminoalkyl-2,5-diketopiperazine having a purity of greater than 80% (i.e., 80 to 100%). In certain embodiments, the disclosed methods provide a 3,6-aminoalkyl-2,5-diketopiperazine having a purity of greater than 90% (i.e., 90 to 100%) or more.

As previously mentioned, in certain embodiments, compounds according to Formula II react to form diketopiperazines of Formula I. In certain such embodiments, the compounds of Formula II react with an amine catalyst. Non-limiting examples of amine catalysts according to the disclosed embodiments include cyclic alkyl amines such as aziridine, and amidoximes such as benzamidoxime. Other catalysts useful according to the methods disclosed herein include: 4-nitrobenzamidoxime, hydroxysuccinimide, p-nitrophenol, and hydroxybenzotriazole.

In embodiments wherein the amine catalyst is a cyclic alkyl amine, the diketopiperazine according to Formula II may be obtained by adding the cyclic α-N protected active amino ester intermediate according to the method discussed by Rosenmund et al., Angew Chem. Internat. Edit. Vol. 9 (1970), the content of which is incorporated by reference as if fully recited herein. In embodiments wherein the amine catalyst is an amidoxime, the diketopiperazine according to Formula II may be obtained by adding the cyclic α-N-protected active amino ester intermediate according to the method discussed by Buijle et al., U.S. Pat. No. 3,407,203, the content of which is hereby incorporate by reference as if fully recited herein.

As mentioned previously, a variety of protecting groups are contemplated for use according to the embodiments disclosed herein. When employing the protecting groups mentioned above, it is advantageous to provide the N-protecting group to the amino acid, prior to cyclization into the cyclic α-N-protected active amino ester intermediates of Compound 3. In certain embodiments according to compound 3, X is C, R is an N-protected alkyl amine. Thus giving compounds such as compound 4

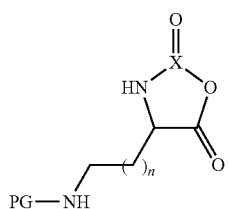

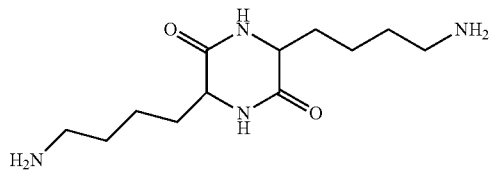

Where PG is trifluoroacetyl, CBz, Boc, acetyl, and n is equal to 1-7. Cyclization of compounds according to structure 4 would thus provide diketopiperazines according to structure 2 above, where PG is trifluoroacetyl, CBz, Boc, acetyl, and n is equal to 1-7.

The cyclic α-N-protected active amino ester intermediates of Compound 4 can be obtained according to a variety of methods. In certain embodiments, the cyclic α-N-protected active amino ester can be obtained via reaction of the N-protected amino acid with phosgene under appropriate conditions. For example, Blacklock et al., provide a procedure for the cyclization N'-(Trifluoroacetyl)-L-lysine (compound 1, PG=TFA, n=3). J. Org. Chem., Vol. 53 (4), 1988, the content of which is hereby incorporated by reference as if fully recited herein. Thus, in certain embodiments, a cyclic α-N-protected active amino ester is obtained by addition of a solution of N-protected amino acid to a cooled solution of phosgene in an organic solvent. In embodiments where X is S, phosgene is replaced with thionyl chloride to give structure such as compound 3.

In certain embodiments, the diketopiperazine synthesized is Compound 5:

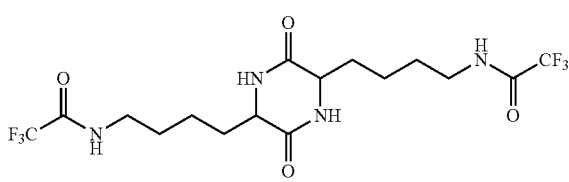

In certain other embodiments, the diketopiperazine synthesized is Compound 11:

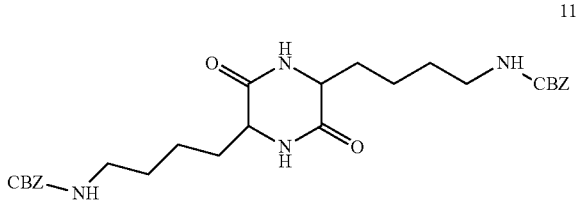

In certain other embodiments, it is contemplated that the PG is removed after formation of the diketopiperazine ring, and optionally, prior to isolation from the reaction. In such embodiments, the diketopiperazine so obtained would correspond to compound 6, PG is H, and n is 3, or:

Examples

FIG. 1 shows a reaction scheme for the production of Compound 11, via a cyclic α-N-protected active amino ester (CBz-Lys-NCA shown in FIG. 1). CBz-Lys-NCA, was synthesized according to the following procedure: triphosgene (26.49 g), CBz-Lys (50.00 g), and tetrahydrofuran (THF) (500 mL) were charged to a 1 L, 4-neck, round bottomed flask fitted with a nitrogen purge, a mechanical stirrer, a condenser and a thermocouple. The reaction mixture was heated to 35-38° C. until clear. The reaction mixture was cooled to ambient temperature, and nitrogen was bubbled through it to remove any excess phosgene. The solvent was then removed in vacuo. The crude product was crystallized from THF (200 mL) and hexane (125 mL). The resulting white solid was isolated by filtration and dried overnight in vacuo. Yield of CBz-Lys-NCA was 48.6 g (89.02%).

Once the CBz-Lys-NCA was obtained, it was used to generate Compound 11 according to the following: benzamidoxime catalyst (3.33 g) and THF (50 mL) were charged to a 250 mL, 3-neck flask fitted with a nitrogen purge, a magnetic stir bar, a thermocouple, and a 60 mL addition funnel. CBz-Lys-NCA (5.00 g) was slurried in THF (50 ml), then added to the catalyst in THF dropwise over 2 hr. The reaction mixture was stirred at ambient temperature overnight, then poured into 100 mL of deionized water. The resulting white solid was isolated by filtration, and dried overnight at 50° C. in vacuo. Crude 11 yield was 3.41 g (79.7%). Pure Compound 11 yield (from CBz-Lys-NCA) was 75.8% after recrystallization.

Figure 2:
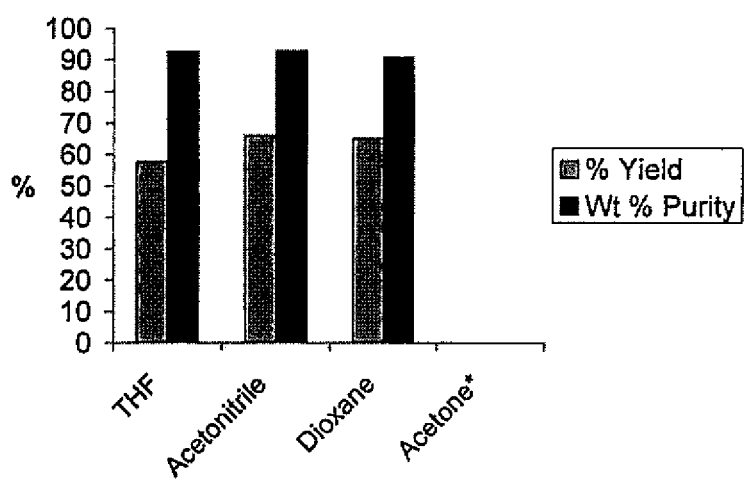
FIG. 2 is a bar graph showing results for a survey of several organic solvents.

A series of solvents (THF, acetonitrile, dioxane and acetone) were evaluated for the step of converting the CBz-Lys-NCA to Compound 11. As can be seen from FIG. 2, acetonitrile, THF, and dioxane gave Compound 11 in comparable yield and purity. However, acetone was judged unacceptable because the reaction produced a viscous yellow material that could not be isolated by filtration.

Figure 3:
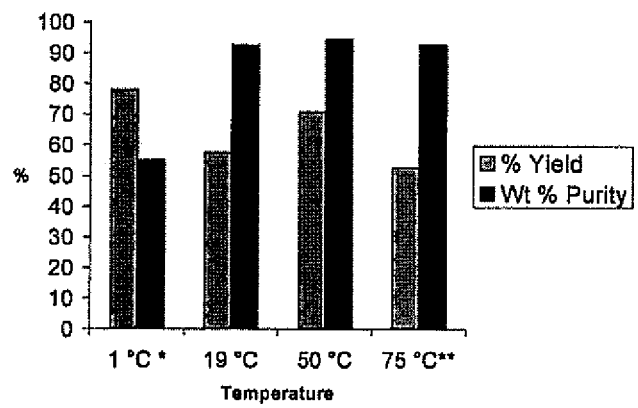
FIG. 3 is a bar graph showing results for several experiments using temperature as a variable.

The effects of temperature (1-75° C.) were also evaluated. THF was used as the reaction solvent, except for the reaction conducted at 75° C., which used acetonitrile. As can be seen from FIG. 3, the highest Compound 11 yield was obtained at 50° C. Purity was unaffected by this elevated temperature. At low temperature (1° C.), high mass recovery was observed, but the quality of the material was low (55.2 wt % purity).

Figure 4:
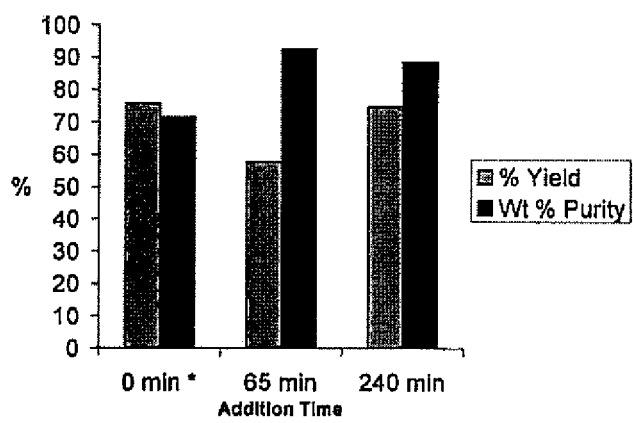
FIG. 4 is a bar graph showing results for several experiments using addition time as a variable.

The rate of CBz-Lys-NCA was varied from 0 to 240 min. As can be seen from FIG. 4, longer addition times gave better Compound 11 yield without negatively impacting purity. When the CBz-Lys-NCA was added in one portion (0 min. addition time), high mass recoveries were observed, but the material quality was low (71.7 wt %).

Figure 5:
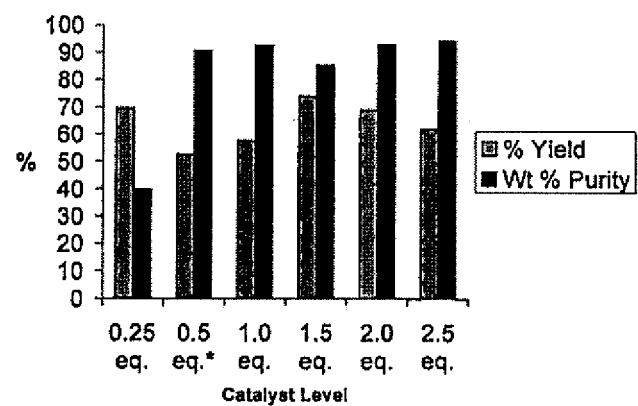
FIG. 5 is a bar graph showing results for several experiments using catalyst level as a variable.

FIG. 5 shows the results of experiments testing the amount of benzamidoxime in the reaction. The benzamidoxime charge was varied from 0.25 to 2.5 eq. (based on the CBz-Lys-NCA charge). FIG. 5 shows that the 1.5 equivalents of benzamidoxime provided the best Compound 11 yield without negatively impacting wt % purity.

Figure 6:
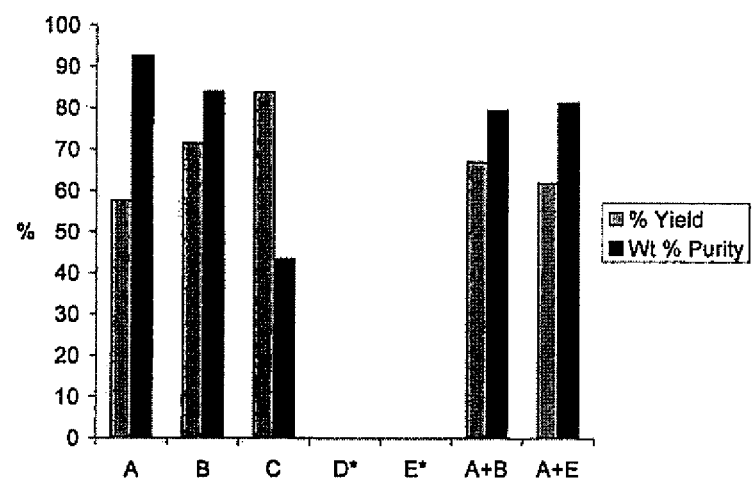
FIG. 6 is a bar graph showing results for several experiments using the particular catalyst as a variable.

FIG. 6 shows the results of experiments testing four additional compounds for their use as catalysts for the general reaction shown in FIG. 1. In FIG. 6, A=benzamidoxime; B=hydroxysuccinimide (HO-Su); C=4-nitrobenzamidoxime; D=p-nitrophenol; E=hydroxybenzotriazole HOBT, note, the reactions using p-nitrophenol and HOBT produced no product. As can be seen from FIG. 6, the use of HO-Su gives Compound 11 in better yield but lower purity than benzamidoxime. The other catalysts screened resulted in either low purity (4-nitrobenzamidoxime) or no product (p-nitrophenol and HOBT). Using 0.2 equivalents of either HOBT or HO-Su as a co-catalyst with 1.0 equivalent of benzamidoxime gave an improved yield of lower-purity Compound 11.

Figure 7:
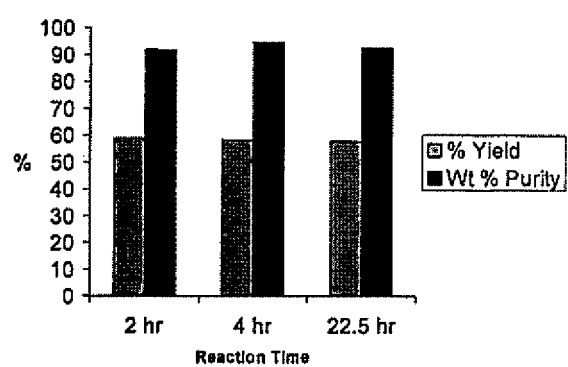
FIG. 7 is a bar graph showing results for several experiments using reaction time as a variable.

FIG. 7 shows the results of experiments wherein the reaction time following addition of CBz-Lys-NCA was varied from 2 to 22.5 hr. As can be seen from FIG. 7, 2 hours was sufficient time for the reaction to proceed to completion, and that very long reaction time did not result in product degradation. All conditions tested gave comparable Compound 11 yield and purity.

The conditions identified as optimal were then tested together in a single reaction. These experimental conditions used THF as solvent, 50° C. reaction temperature, and CBz-Lys-NCA addition over 4 hrs, followed by an additional 2 hours of stirring prior to product isolation. Using these conditions, recrystallized Compound 11 was recovered in 55.8% yield, with a purity of 97.75 wt %. Unwanted oligomer formation was not observed using these conditions.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar references used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of any and all Markush groups used in the appended claims.

The invention claimed is:

1. A method for the synthesis of a N-protected-bis-3,6-aminoalkyl-2,5-diketopiperazine, the method comprising:
adding a cyclic α-N protected active amino ester according to Formula II

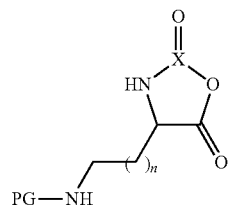

Formula II wherein PG is selected from the group consisting of amide forming protecting groups and carbamate protecting groups; and
wherein n is from 1 to 8;
to a mixture of an amine catalyst in an organic solvent, wherein the amine catalyst is present in amount of 0.25 to 2.5 eq based on the amount of cyclic α-N protected active amino ester; and
heating the mixture after adding the cyclic α-N protected active amino ester.

2. The method of claim 1, wherein PG is trifluoroacetyl.

3. The method of claim 1, wherein n is 3.

4. The method of claim 1, wherein the amine catalyst is aziridine.

5. The method of claim 1, wherein the amine catalyst is an amidoxime.

6. The method of claim 1, wherein the amine catalyst is benzamidoxime.

7. The method of claim 1, wherein the amine catalyst is present in an amount of 1 to 2 eq based on the amount of cyclic α-N protected active amino ester.

8. The method of claim 1, wherein the amine catalyst is present in an amount of 1.5 eq based on the amount of cyclic α-N protected active amino ester.

9. The method of claim 1, wherein the mixture further comprises a second catalyst.

10. The method of claim 1, wherein the organic solvent is ethanol and the amine catalyst is aziridine.

11. The method of claim 1, wherein the organic solvent is THF and the amine catalyst is aziridine.

12. The method of claim 1, wherein PG is acetyl.

13. The method of claim 1, wherein PG is Boc.

14. The method of claim 1, wherein PG is CBz.

15. A method for the synthesis of a N-protected-bis-3,6-aminoalkyl-2,5-diketopiperazine, the method comprising: adding a cyclic α-N protected active amino ester according to Formula II

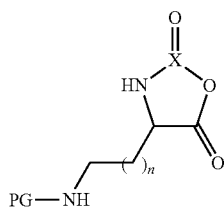

Formula II wherein PG is trifluoroacetyl; and
wherein n is from 1 to 8;
  to a mixture of an amine catalyst in an organic solvent, wherein the amine catalyst is present in amount of 1 to 2 eq based on the amount of cyclic α-N protected active amino ester and heating the mixture after adding the cyclic α-N protected active amino ester.

16. The method of claim 15, wherein the organic solvent is selected from ethanol and THF and the amine catalyst is aziridine.

17. The method of claim 15, wherein the organic solvent is selected from ethanol and THF and the amine catalyst is benzamidoxime.

18. The method of claim 15, wherein n is 3.

19. The method of claim 15, wherein the amine catalyst is present in amount of 1.5 eq based on the amount of cyclic α-N protected active amino ester.

20. A method for the synthesis of a N-protected-bis-3,6-aminoalkyl-2,5-diketopiperazine, the method comprising: adding a cyclic α-N protected active amino ester according to Formula II

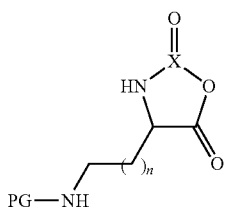

Formula II wherein PG is selected from the group consisting of amide forming protecting groups and carbamate protecting groups; and
wherein n is from 1 to 8;
  to a mixture of an amine catalyst and a second catalyst in an organic solvent,
  wherein the amine catalyst is present in amount of 0.25 to 2.5 eq based on the amount of cyclic α-N protected active amino ester.

* * * * *